United States Patent
McCartney

(10) Patent No.: US 9,788,826 B2
(45) Date of Patent: Oct. 17, 2017

(54) FILAMENTARY FIXATION DEVICE AND ASSEMBLY AND METHOD OF ASSEMBLY, MANUFACTURE AND USE

(71) Applicant: Howmedica Osteonics Corp., Mahwah, NJ (US)

(72) Inventor: Charles McCartney, Denver, CO (US)

(73) Assignee: Howmedica Osteonics Corp., Mahwah, NJ (US)

( * ) Notice: Subject to any disclaimer, the term of this patent is extended or adjusted under 35 U.S.C. 154(b) by 697 days.

(21) Appl. No.: 13/792,982

(22) Filed: Mar. 11, 2013

(65) Prior Publication Data

US 2014/0257382 A1    Sep. 11, 2014

(51) Int. Cl.
    *A61B 17/04*    (2006.01)

(52) U.S. Cl.
    CPC ...... *A61B 17/0401* (2013.01); *A61B 17/0485* (2013.01); *A61B 2017/0406* (2013.01); *A61B 2017/0458* (2013.01); *A61B 2017/0475* (2013.01)

(58) Field of Classification Search
    CPC ........ A61B 17/0401; A61B 2017/0458; A61B 2017/00526; A61B 2017/0414; A61B 2017/0445
    See application file for complete search history.

(56) References Cited

U.S. PATENT DOCUMENTS

| | | |
|---|---|---|
| 749,624 A | 1/1904 | McCullough |
| 1,308,798 A | 7/1919 | Masland |
| 1,624,530 A | 4/1927 | Caruso |
| 2,073,903 A | 3/1937 | O'Neil |
| 2,267,925 A | 12/1941 | Johnston |
| 2,382,019 A | 8/1945 | Miller |
| 2,494,229 A | 1/1950 | Collison |
| 2,515,365 A | 7/1950 | Zublin |
| 2,547,571 A | 4/1951 | Ettinger |
| 2,808,632 A | 10/1957 | Cline |
| 2,833,284 A | 5/1958 | Springer |
| 3,384,085 A | 5/1968 | Hall |

(Continued)

FOREIGN PATENT DOCUMENTS

| | | |
|---|---|---|
| DE | 3131496 A1 | 2/1983 |
| DE | 4231101 A1 | 3/1994 |

(Continued)

OTHER PUBLICATIONS

Extended European Search Report for Application No. EP14157129 dated Oct. 9, 2014.

(Continued)

*Primary Examiner* — Corrine McDermott
*Assistant Examiner* — Tin Nguyen
(74) *Attorney, Agent, or Firm* — Lerner, David, Littenberg, Krumholz & Mentlik, LLP

(57) ABSTRACT

The present invention, in one embodiment, includes a method of assembling a filamentary fixation device including obtaining a filamentary sleeve having a pathway therethrough, and a loading member and retriever member each positioned through at least a portion of the pathway, engaging a working suture with the retriever member, positioning at least a portion of the working suture in the pathway using the retriever member, and engaging the working suture with the loading member.

7 Claims, 8 Drawing Sheets

(56) References Cited

U.S. PATENT DOCUMENTS

| | | |
|---|---|---|
| 3,461,875 A | 8/1969 | Hall |
| 3,554,192 A | 1/1971 | Isberner |
| 3,580,256 A | 5/1971 | Wilkinson et al. |
| 3,608,095 A | 9/1971 | Barry |
| 3,659,597 A | 5/1972 | Wolfers |
| 3,750,671 A | 8/1973 | Hedrick |
| 3,810,456 A | 5/1974 | Karman |
| 3,845,772 A | 11/1974 | Smith |
| 3,867,932 A | 2/1975 | Huene |
| 3,892,232 A | 7/1975 | Neufeld |
| 3,976,079 A | 8/1976 | Samuels et al. |
| 4,265,231 A | 5/1981 | Scheller, Jr. et al. |
| 4,328,839 A | 5/1982 | Lyons et al. |
| 4,483,562 A | 11/1984 | Schoolman |
| 4,489,446 A | 12/1984 | Reed |
| 4,541,423 A | 9/1985 | Barber |
| 4,608,972 A | 9/1986 | Small |
| 4,611,515 A | 9/1986 | Marbourg, Jr. |
| 4,646,738 A | 3/1987 | Trott |
| 4,706,659 A | 11/1987 | Matthews et al. |
| 4,741,330 A | 5/1988 | Hayhurst |
| 4,748,872 A | 6/1988 | Brown |
| 4,751,922 A | 6/1988 | DiPietropolo |
| 4,781,182 A | 11/1988 | Purnell et al. |
| 4,823,780 A | 4/1989 | Odensten et al. |
| 4,872,451 A | 10/1989 | Moore et al. |
| 4,946,462 A | 8/1990 | Watanabe |
| 5,002,546 A | 3/1991 | Romano |
| 5,021,059 A | 6/1991 | Kensey et al. |
| 5,030,219 A | 7/1991 | Matsen, III et al. |
| 5,037,422 A | 8/1991 | Hayhurst et al. |
| 5,037,423 A | 8/1991 | Kenna |
| 5,061,277 A | 10/1991 | Carpentier et al. |
| 5,064,431 A | 11/1991 | Gilbertson et al. |
| 5,122,134 A | 6/1992 | Borzone et al. |
| 5,123,914 A | 6/1992 | Cope |
| 5,133,720 A | 7/1992 | Greenberg |
| 5,139,520 A | 8/1992 | Rosenberg |
| 5,141,520 A | 8/1992 | Goble et al. |
| 5,163,940 A | 11/1992 | Bourque |
| 5,190,548 A | 3/1993 | Davis |
| 5,203,595 A | 4/1993 | Borzone et al. |
| 5,203,787 A | 4/1993 | Noblitt et al. |
| RE34,293 E | 6/1993 | Goble et al. |
| 5,234,435 A | 8/1993 | Seagrave, Jr. |
| 5,259,846 A | 11/1993 | Granger et al. |
| 5,269,785 A | 12/1993 | Bonutti |
| 5,269,809 A | 12/1993 | Hayhurst et al. |
| 5,300,077 A | 4/1994 | Howell |
| 5,314,429 A | 5/1994 | Goble |
| 5,320,115 A | 6/1994 | Kenna |
| 5,320,626 A | 6/1994 | Schmieding |
| 5,324,308 A | 6/1994 | Pierce |
| 5,350,383 A | 9/1994 | Schmieding et al. |
| RE34,762 E | 10/1994 | Goble et al. |
| 5,374,269 A | 12/1994 | Rosenberg |
| 5,385,567 A | 1/1995 | Goble |
| 5,391,170 A | 2/1995 | McGuire et al. |
| 5,391,171 A | 2/1995 | Schmieding |
| RE34,871 E | 3/1995 | McGuire et al. |
| 5,395,188 A | 3/1995 | Bailey et al. |
| 5,403,317 A | 4/1995 | Bonutti |
| 5,403,348 A | 4/1995 | Bonutti |
| 5,405,359 A | 4/1995 | Pierce |
| 5,409,494 A | 4/1995 | Morgan |
| 5,417,691 A | 5/1995 | Hayhurst |
| 5,423,860 A | 6/1995 | Lizardi et al. |
| 5,437,677 A | 8/1995 | Shearer et al. |
| 5,441,502 A | 8/1995 | Bartlett |
| 5,443,482 A | 8/1995 | Stone et al. |
| 5,458,604 A | 10/1995 | Schmieding |
| 5,464,407 A | 11/1995 | McGuire |
| 5,464,425 A | 11/1995 | Skiba |
| 5,464,426 A | 11/1995 | Bonutti |
| 5,466,243 A | 11/1995 | Schmieding et al. |
| 5,472,452 A | 12/1995 | Trott |
| 5,486,197 A | 1/1996 | Le et al. |
| 5,488,761 A | 2/1996 | Leone |
| 5,496,348 A | 3/1996 | Bonutti |
| 5,505,736 A | 4/1996 | Reimels et al. |
| 5,520,693 A | 5/1996 | McGuire et al. |
| 5,520,700 A | 5/1996 | Beyar et al. |
| 5,522,846 A | 6/1996 | Bonutti |
| 5,527,316 A | 6/1996 | Stone et al. |
| 5,527,343 A | 6/1996 | Bonutti |
| 5,529,580 A | 6/1996 | Kusunoki et al. |
| 5,531,759 A | 7/1996 | Kensey et al. |
| 5,534,012 A | 7/1996 | Bonutti |
| 5,545,178 A | 8/1996 | Kensey et al. |
| 5,548,862 A | 8/1996 | Curtis |
| 5,569,269 A | 10/1996 | Hart et al. |
| 5,569,306 A | 10/1996 | Thal |
| 5,570,706 A | 11/1996 | Howell |
| 5,571,111 A | 11/1996 | Aboczky |
| 5,573,542 A | 11/1996 | Stevens |
| 5,575,819 A | 11/1996 | Amis |
| 5,584,695 A | 12/1996 | Lal Sachdeva et al. |
| 5,584,835 A | 12/1996 | Greenfield |
| 5,601,557 A | 2/1997 | Hayhurst |
| 5,601,561 A | 2/1997 | Terry et al. |
| 5,618,314 A | 4/1997 | Harwin et al. |
| 5,645,545 A | 7/1997 | Bryant |
| 5,645,589 A | 7/1997 | Li |
| 5,647,874 A | 7/1997 | Hayhurst |
| 5,649,963 A | 7/1997 | McDevitt |
| 5,658,313 A | 8/1997 | Thal |
| 5,662,658 A | 9/1997 | Wenstrom, Jr. |
| 5,665,110 A | 9/1997 | Chervitz et al. |
| 5,665,111 A | 9/1997 | Ray et al. |
| 5,665,112 A | 9/1997 | Thal |
| 5,667,509 A | 9/1997 | Westin |
| 5,674,279 A | 10/1997 | Wright et al. |
| 5,681,320 A | 10/1997 | McGuire |
| 5,681,352 A | 10/1997 | Clancy, III et al. |
| 5,683,401 A | 11/1997 | Schmieding et al. |
| 5,683,418 A | 11/1997 | Luscombe et al. |
| 5,683,419 A | 11/1997 | Thal |
| 5,690,676 A | 11/1997 | DiPoto et al. |
| 5,690,677 A | 11/1997 | Schmieding et al. |
| 5,695,513 A | 12/1997 | Johnson et al. |
| 5,702,397 A | 12/1997 | Goble et al. |
| 5,709,708 A | 1/1998 | Thal |
| 5,713,905 A | 2/1998 | Goble et al. |
| 5,716,397 A | 2/1998 | Myers |
| 5,718,717 A | 2/1998 | Bonutti |
| 5,720,765 A | 2/1998 | Thal |
| 5,725,541 A | 3/1998 | Anspach, III et al. |
| 5,725,557 A | 3/1998 | Gatturna et al. |
| 5,728,136 A | 3/1998 | Thal |
| 5,732,606 A | 3/1998 | Chiang |
| 5,733,306 A | 3/1998 | Bonutti |
| 5,733,307 A | 3/1998 | Dinsdale |
| 5,749,899 A | 5/1998 | Bardin et al. |
| 5,755,724 A | 5/1998 | Yoon |
| 5,755,731 A | 5/1998 | Grinberg |
| 5,766,221 A | 6/1998 | Benderev et al. |
| 5,782,862 A | 7/1998 | Bonutti |
| 5,782,864 A | 7/1998 | Lizardi |
| 5,782,866 A | 7/1998 | Wenstrom, Jr. |
| 5,797,918 A | 8/1998 | McGuire et al. |
| 5,810,825 A | 9/1998 | Huebner |
| 5,814,056 A | 9/1998 | Prosst et al. |
| 5,836,953 A | 11/1998 | Yoon |
| 5,851,208 A | 12/1998 | Trott |
| 5,885,294 A | 3/1999 | Pedlick et al. |
| 5,888,034 A | 3/1999 | Greenberg |
| 5,891,168 A | 4/1999 | Thal |
| 5,897,574 A | 4/1999 | Bonutti |
| 5,906,626 A | 5/1999 | Carrillo |
| 5,921,986 A | 7/1999 | Bonutti |
| 5,928,244 A | 7/1999 | Tovey et al. |
| 5,941,139 A | 8/1999 | Vodehnal |
| 5,948,002 A | 9/1999 | Bonutti |
| 5,951,559 A | 9/1999 | Burkhart |

(56) References Cited

U.S. PATENT DOCUMENTS

| | | |
|---|---|---|
| 5,968,078 A | 10/1999 | Grotz |
| 5,980,539 A | 11/1999 | Kontos |
| 5,980,558 A | 11/1999 | Wiley |
| 5,980,559 A | 11/1999 | Bonutti |
| 5,989,252 A | 11/1999 | Fumex |
| 5,993,451 A | 11/1999 | Burkhart |
| 5,997,541 A | 12/1999 | Schenk |
| 6,007,566 A | 12/1999 | Wenstrom, Jr. |
| 6,007,567 A | 12/1999 | Bonutti |
| 6,010,515 A | 1/2000 | Swain et al. |
| 6,010,525 A | 1/2000 | Bonutti et al. |
| 6,019,767 A | 2/2000 | Howell |
| 6,024,758 A | 2/2000 | Thal |
| 6,045,574 A | 4/2000 | Thal |
| 6,053,922 A | 4/2000 | Krause et al. |
| 6,068,642 A | 5/2000 | Johnson et al. |
| 6,077,292 A | 6/2000 | Bonutti |
| 6,120,511 A | 9/2000 | Chan |
| 6,143,017 A | 11/2000 | Thal |
| 6,146,385 A | 11/2000 | Torrie et al. |
| 6,152,949 A | 11/2000 | Bonutti |
| 6,156,039 A | 12/2000 | Thal |
| 6,156,056 A | 12/2000 | Kearns et al. |
| 6,159,234 A | 12/2000 | Bonutti et al. |
| 6,183,461 B1 | 2/2001 | Matsuura et al. |
| 6,187,011 B1 | 2/2001 | Torrie |
| 6,189,422 B1 | 2/2001 | Stihl |
| 6,210,415 B1 | 4/2001 | Bester |
| 6,224,608 B1 | 5/2001 | Ciccolella et al. |
| 6,245,081 B1 | 6/2001 | Bowman et al. |
| 6,254,604 B1 | 7/2001 | Howell |
| 6,306,138 B1 | 10/2001 | Clark et al. |
| 6,306,159 B1 | 10/2001 | Schwartz et al. |
| 6,343,482 B1 | 2/2002 | Endo et al. |
| 6,352,538 B2 | 3/2002 | McGuire et al. |
| 6,358,253 B1 | 3/2002 | Torrie et al. |
| 6,419,678 B1 | 7/2002 | Asfora |
| 6,419,684 B1 | 7/2002 | Heisler et al. |
| 6,436,100 B1 | 8/2002 | Berger |
| 6,436,124 B1 | 8/2002 | Anderson et al. |
| 6,440,138 B1 | 8/2002 | Reiley et al. |
| 6,440,141 B1 | 8/2002 | Philippon |
| 6,447,518 B1 | 9/2002 | Krause et al. |
| 6,464,713 B2 | 10/2002 | Bonutti |
| 6,475,230 B1 | 11/2002 | Bonutti et al. |
| 6,478,800 B1 | 11/2002 | Fraser et al. |
| 6,485,504 B1 | 11/2002 | Johnson et al. |
| 6,500,195 B2 | 12/2002 | Bonutti |
| RE37,963 E | 1/2003 | Thal |
| 6,508,830 B2 | 1/2003 | Steiner |
| 6,511,498 B1 | 1/2003 | Fumex |
| 6,517,578 B2 | 2/2003 | Hein |
| 6,544,281 B2 | 4/2003 | ElAttrache et al. |
| 6,558,386 B1 | 5/2003 | Cragg |
| 6,558,390 B2 | 5/2003 | Cragg |
| 6,569,187 B1 | 5/2003 | Bonutti et al. |
| 6,572,635 B1 | 6/2003 | Bonutti |
| 6,575,979 B1 | 6/2003 | Cragg |
| 6,610,080 B2 | 8/2003 | Morgan |
| 6,635,073 B2 | 10/2003 | Bonutti |
| 6,638,279 B2 | 10/2003 | Bonutti |
| 6,638,283 B2 | 10/2003 | Thal |
| 6,641,597 B2 | 11/2003 | Burkhart et al. |
| 6,660,023 B2 | 12/2003 | McDevitt et al. |
| 6,712,822 B2 | 3/2004 | Re et al. |
| 6,716,234 B2 | 4/2004 | Grafton et al. |
| 6,740,090 B1 | 5/2004 | Cragg et al. |
| 6,780,188 B2 | 8/2004 | Clark et al. |
| 6,790,210 B1 | 9/2004 | Cragg et al. |
| 6,805,697 B1 | 10/2004 | Helm et al. |
| 6,824,552 B2 | 11/2004 | Robison et al. |
| 6,830,570 B1 | 12/2004 | Frey et al. |
| 6,863,672 B2 | 3/2005 | Reiley et al. |
| 6,878,150 B1 | 4/2005 | McGuire et al. |
| 6,887,259 B2 | 5/2005 | Lizardi |
| 6,893,445 B1 | 5/2005 | Revie et al. |
| 6,899,716 B2 | 5/2005 | Cragg |
| 6,921,403 B2 | 7/2005 | Cragg et al. |
| 6,923,811 B1 | 8/2005 | Carl et al. |
| 6,923,814 B1 | 8/2005 | Hildebrand et al. |
| 6,936,052 B2 | 8/2005 | Gellman et al. |
| 6,955,683 B2 | 10/2005 | Bonutti |
| 6,960,214 B2 | 11/2005 | Burkinshaw |
| 6,991,636 B2 | 1/2006 | Rose |
| 6,994,719 B2 | 2/2006 | Grafton |
| 6,995,683 B2 | 2/2006 | Smithson et al. |
| 7,008,431 B2 | 3/2006 | Simonson |
| 7,025,770 B2 | 4/2006 | McGuire et al. |
| 7,029,490 B2 | 4/2006 | Grafton et al. |
| 7,048,754 B2 | 5/2006 | Martin et al. |
| 7,060,073 B2 | 6/2006 | Frey et al. |
| 7,067,132 B2 | 6/2006 | Grabstein et al. |
| 7,077,863 B2 | 7/2006 | Schmieding et al. |
| 7,087,058 B2 | 8/2006 | Cragg |
| 7,087,073 B2 | 8/2006 | Bonutti |
| 7,204,839 B2 | 4/2007 | Dreyfuss et al. |
| 7,217,279 B2 | 5/2007 | Reese |
| 7,217,290 B2 | 5/2007 | Bonutti |
| 7,241,297 B2 | 7/2007 | Shaolian et al. |
| 7,258,692 B2 | 8/2007 | Thelen et al. |
| 7,261,016 B2 | 8/2007 | Miller |
| 7,309,338 B2 | 12/2007 | Cragg |
| 7,326,215 B2 | 2/2008 | Myers et al. |
| 7,331,263 B2 | 2/2008 | Erickson et al. |
| 7,381,213 B2 | 6/2008 | Lizardi |
| 7,488,322 B2 | 2/2009 | Brunnett et al. |
| 7,488,329 B2 | 2/2009 | Thelen et al. |
| 7,494,490 B2 | 2/2009 | Justin |
| 7,500,977 B2 | 3/2009 | Assell et al. |
| 7,503,920 B2 | 3/2009 | Siegal |
| 7,520,898 B2 | 4/2009 | Re et al. |
| 7,563,266 B2 | 7/2009 | Camino et al. |
| 7,578,836 B2 | 8/2009 | Justin et al. |
| 7,585,300 B2 | 9/2009 | Cha |
| 7,601,155 B2 | 10/2009 | Petersen |
| 7,601,165 B2 | 10/2009 | Stone |
| 7,604,636 B1 | 10/2009 | Walters et al. |
| 7,608,098 B1 | 10/2009 | Stone et al. |
| 7,611,521 B2 | 11/2009 | Lubbers et al. |
| 7,621,912 B2 | 11/2009 | Harms et al. |
| 7,621,940 B2 | 11/2009 | Harms et al. |
| 7,651,515 B2 | 1/2010 | Mack et al. |
| 7,658,751 B2 | 2/2010 | Stone et al. |
| 7,666,189 B2 | 2/2010 | Gerber et al. |
| 7,678,134 B2 | 3/2010 | Schmieding et al. |
| 7,749,250 B2 | 7/2010 | Stone et al. |
| 7,776,049 B1 | 8/2010 | Curran et al. |
| 7,857,830 B2 | 12/2010 | Stone et al. |
| 7,879,037 B2 | 2/2011 | Brunnett et al. |
| 7,892,256 B2 | 2/2011 | Grafton et al. |
| 7,905,903 B2 | 3/2011 | Stone et al. |
| 7,905,904 B2 | 3/2011 | Stone et al. |
| 7,909,851 B2 | 3/2011 | Stone et al. |
| 7,914,539 B2 | 3/2011 | Stone et al. |
| 7,918,874 B2 | 4/2011 | Siegal |
| 7,959,650 B2 | 6/2011 | Kaiser et al. |
| 7,981,117 B2 | 7/2011 | Newton et al. |
| 7,993,369 B2 | 8/2011 | Dreyfuss |
| 8,002,733 B2 | 8/2011 | Kraft et al. |
| 8,043,253 B2 | 10/2011 | Kraft et al. |
| 8,057,500 B2 | 11/2011 | Mitusina |
| 8,088,130 B2 | 1/2012 | Kaiser et al. |
| 8,114,088 B2 | 2/2012 | Miller |
| 8,118,836 B2 | 2/2012 | Denham et al. |
| 8,123,750 B2 | 2/2012 | Norton et al. |
| 8,128,640 B2 | 3/2012 | Harris et al. |
| 8,128,658 B2 | 3/2012 | Kaiser et al. |
| 8,128,669 B2 | 3/2012 | Bonutti |
| 8,133,231 B2 | 3/2012 | Martinek et al. |
| 8,137,382 B2 | 3/2012 | Denham et al. |
| 8,147,514 B2 | 4/2012 | Bonutti |
| 8,172,846 B2 | 5/2012 | Brunnett et al. |
| 8,231,654 B2 | 7/2012 | Kaiser et al. |
| 8,241,305 B2 | 8/2012 | Stone |

(56) References Cited

U.S. PATENT DOCUMENTS

| | | |
|---|---|---|
| 8,273,106 B2 | 9/2012 | Stone et al. |
| 8,292,921 B2 | 10/2012 | Stone et al. |
| 8,298,262 B2 | 10/2012 | Stone et al. |
| 8,303,604 B2 | 11/2012 | Stone et al. |
| 8,317,825 B2 | 11/2012 | Stone |
| 8,337,525 B2 | 12/2012 | Stone et al. |
| 8,361,113 B2 | 1/2013 | Stone et al. |
| 8,409,253 B2 | 4/2013 | Stone et al. |
| 8,562,645 B2 | 10/2013 | Stone et al. |
| 8,801,800 B2 | 8/2014 | Bagga et al. |
| 8,814,905 B2 | 8/2014 | Sengun et al. |
| 8,821,543 B2 | 9/2014 | Hernandez et al. |
| 8,821,544 B2 | 9/2014 | Sengun et al. |
| 8,821,545 B2 | 9/2014 | Sengun |
| 9,370,350 B2 | 6/2016 | Norton |
| 9,445,803 B2 | 9/2016 | Marchand et al. |
| 9,451,938 B2 | 9/2016 | Overes et al. |
| 2002/0019635 A1 | 2/2002 | Wenstrom et al. |
| 2002/0188301 A1 | 12/2002 | Dallara et al. |
| 2003/0032961 A1 | 2/2003 | Pelo et al. |
| 2003/0176919 A1 | 9/2003 | Schmieding |
| 2003/0195565 A1 | 10/2003 | Bonutti |
| 2003/0220646 A1 | 11/2003 | Thelen et al. |
| 2003/0233098 A1 | 12/2003 | Markworth |
| 2004/0010264 A1 | 1/2004 | Acker et al. |
| 2004/0010287 A1 | 1/2004 | Bonutti |
| 2004/0030346 A1 | 2/2004 | Frey et al. |
| 2004/0073227 A1 | 4/2004 | Dreyfuss et al. |
| 2004/0073306 A1 | 4/2004 | Eichhorn et al. |
| 2004/0092933 A1 | 5/2004 | Shaolian et al. |
| 2004/0193217 A1 | 9/2004 | Lubbers et al. |
| 2004/0260300 A1 | 12/2004 | Gorensek et al. |
| 2004/0267277 A1 | 12/2004 | Zannis et al. |
| 2005/0015153 A1 | 1/2005 | Goble et al. |
| 2005/0033362 A1 | 2/2005 | Grafton |
| 2005/0070906 A1 | 3/2005 | Clark et al. |
| 2005/0137600 A1 | 6/2005 | Jacobs et al. |
| 2005/0137601 A1 | 6/2005 | Assell et al. |
| 2005/0143741 A1 | 6/2005 | Timmermans et al. |
| 2005/0177168 A1 | 8/2005 | Brunnett et al. |
| 2005/0187537 A1 | 8/2005 | Loeb et al. |
| 2005/0203527 A1 | 9/2005 | Carrison et al. |
| 2005/0228399 A1 | 10/2005 | Kubo et al. |
| 2005/0251159 A1 | 11/2005 | Ewers et al. |
| 2005/0251208 A1 | 11/2005 | Elmer et al. |
| 2005/0283156 A1 | 12/2005 | Schmieding et al. |
| 2005/0288710 A1 | 12/2005 | Fallin et al. |
| 2006/0001518 A1 | 1/2006 | Hayashi et al. |
| 2006/0004369 A1 | 1/2006 | Patel et al. |
| 2006/0015108 A1 | 1/2006 | Bonutti |
| 2006/0074434 A1 | 4/2006 | Wenstrom et al. |
| 2006/0079904 A1 | 4/2006 | Thal |
| 2006/0100631 A1 | 5/2006 | Sullivan et al. |
| 2006/0155329 A1 | 7/2006 | Grafton et al. |
| 2006/0178748 A1 | 8/2006 | Dinger et al. |
| 2006/0189993 A1 | 8/2006 | Stone |
| 2006/0190042 A1 | 8/2006 | Stone et al. |
| 2006/0212055 A1 | 9/2006 | Karabey et al. |
| 2006/0247641 A1 | 11/2006 | Re et al. |
| 2006/0247642 A1 | 11/2006 | Stone et al. |
| 2006/0282085 A1 | 12/2006 | Stone et al. |
| 2006/0293689 A1 | 12/2006 | Miller et al. |
| 2007/0010843 A1 | 1/2007 | Green |
| 2007/0010857 A1 | 1/2007 | Sugimoto et al. |
| 2007/0032800 A1 | 2/2007 | Ortiz et al. |
| 2007/0093840 A1 | 4/2007 | Pacelli et al. |
| 2007/0185532 A1 | 8/2007 | Stone et al. |
| 2007/0191853 A1 | 8/2007 | Stone |
| 2007/0213734 A1 | 9/2007 | Bleich et al. |
| 2007/0213735 A1 | 9/2007 | Saadat et al. |
| 2007/0225721 A1 | 9/2007 | Thelen et al. |
| 2007/0233151 A1 | 10/2007 | Chudik |
| 2007/0255317 A1 | 11/2007 | Fanton et al. |
| 2007/0260259 A1 | 11/2007 | Fanton et al. |
| 2007/0288023 A1 | 12/2007 | Pellegrino et al. |
| 2007/0288031 A1 | 12/2007 | Dreyfuss et al. |
| 2008/0004659 A1 | 1/2008 | Burkhart et al. |
| 2008/0009904 A1 | 1/2008 | Bourque et al. |
| 2008/0027446 A1 | 1/2008 | Stone et al. |
| 2008/0027457 A1 | 1/2008 | Dienst et al. |
| 2008/0046009 A1 | 2/2008 | Albertorio et al. |
| 2008/0058816 A1 | 3/2008 | Philippon et al. |
| 2008/0065080 A1 | 3/2008 | Assell et al. |
| 2008/0065092 A1 | 3/2008 | Assell et al. |
| 2008/0065114 A1 | 3/2008 | Stone et al. |
| 2008/0071282 A1 | 3/2008 | Assell et al. |
| 2008/0082127 A1 | 4/2008 | Stone et al. |
| 2008/0082128 A1 | 4/2008 | Stone |
| 2008/0109037 A1 | 5/2008 | Steiner et al. |
| 2008/0114364 A1 | 5/2008 | Goldin et al. |
| 2008/0114399 A1 | 5/2008 | Bonutti |
| 2008/0132932 A1 | 6/2008 | Hoeppner et al. |
| 2008/0140078 A1 | 6/2008 | Nelson et al. |
| 2008/0140092 A1 | 6/2008 | Stone et al. |
| 2008/0140116 A1 | 6/2008 | Bonutti |
| 2008/0147063 A1 | 6/2008 | Cauldwell et al. |
| 2008/0147064 A1 | 6/2008 | Cauldwell et al. |
| 2008/0154275 A1 | 6/2008 | Assell et al. |
| 2008/0161814 A1 | 7/2008 | McAllister et al. |
| 2008/0167660 A1 | 7/2008 | Moreau et al. |
| 2008/0188854 A1 | 8/2008 | Moser |
| 2008/0188935 A1 | 8/2008 | Saylor et al. |
| 2008/0249481 A1 | 10/2008 | Crainich et al. |
| 2008/0255613 A1 | 10/2008 | Kaiser et al. |
| 2008/0262544 A1 | 10/2008 | Burkhart |
| 2008/0275431 A1 | 11/2008 | Stone et al. |
| 2008/0306483 A1 | 12/2008 | Iannarone |
| 2008/0312689 A1 | 12/2008 | Denham et al. |
| 2008/0319478 A1 | 12/2008 | Foerster et al. |
| 2009/0012526 A1 | 1/2009 | Fletcher |
| 2009/0018654 A1 | 1/2009 | Schmieding et al. |
| 2009/0024130 A1 | 1/2009 | Lombardo |
| 2009/0054928 A1 | 2/2009 | Denham et al. |
| 2009/0062854 A1 | 3/2009 | Kaiser et al. |
| 2009/0076514 A1 | 3/2009 | Haines |
| 2009/0082805 A1 | 3/2009 | Kaiser et al. |
| 2009/0099554 A1 | 4/2009 | Forster et al. |
| 2009/0105775 A1 | 4/2009 | Mitchell et al. |
| 2009/0131940 A1 | 5/2009 | Brunnett et al. |
| 2009/0138015 A1 | 5/2009 | Conner et al. |
| 2009/0138042 A1 | 5/2009 | Thal |
| 2009/0143784 A1 | 6/2009 | Petersen et al. |
| 2009/0149858 A1 | 6/2009 | Fanelli et al. |
| 2009/0157081 A1 | 6/2009 | Homan et al. |
| 2009/0160112 A1 | 6/2009 | Ostrovsky |
| 2009/0171359 A1 | 7/2009 | Sterrett |
| 2009/0192468 A1 | 7/2009 | Stone |
| 2009/0194446 A1 | 8/2009 | Miller et al. |
| 2009/0198258 A1 | 8/2009 | Workman |
| 2009/0216238 A1 | 8/2009 | Stark |
| 2009/0216243 A1 | 8/2009 | Re |
| 2009/0234386 A1 | 9/2009 | Dean et al. |
| 2009/0234451 A1 | 9/2009 | Manderson |
| 2009/0240104 A1 | 9/2009 | Ogdahl et al. |
| 2009/0248029 A1 | 10/2009 | Paulos |
| 2009/0265002 A1 | 10/2009 | Re et al. |
| 2009/0306671 A1 | 12/2009 | McCormack et al. |
| 2009/0306711 A1 | 12/2009 | Stone et al. |
| 2009/0312763 A1 | 12/2009 | McCormack et al. |
| 2009/0312776 A1 | 12/2009 | Kaiser et al. |
| 2009/0312792 A1 | 12/2009 | Fallin et al. |
| 2009/0312793 A1 | 12/2009 | Huxel et al. |
| 2009/0318961 A1 | 12/2009 | Stone et al. |
| 2009/0326538 A1 | 12/2009 | Sennett et al. |
| 2010/0049196 A1 | 2/2010 | Re |
| 2010/0049202 A1 | 2/2010 | Re |
| 2010/0057045 A1 | 3/2010 | Albritton, IV et al. |
| 2010/0076440 A1 | 3/2010 | Pamichev et al. |
| 2010/0082033 A1 | 4/2010 | Germain |
| 2010/0087857 A1 | 4/2010 | Stone et al. |
| 2010/0121332 A1 | 5/2010 | Crainich et al. |
| 2010/0121333 A1 | 5/2010 | Crainich et al. |
| 2010/0145384 A1 | 6/2010 | Stone et al. |
| 2010/0152739 A1 | 6/2010 | Sidebotham et al. |

(56) References Cited

U.S. PATENT DOCUMENTS

| | | |
|---|---|---|
| 2010/0185238 A1 | 7/2010 | Cauldwell et al. |
| 2010/0185283 A1 | 7/2010 | Baird et al. |
| 2010/0191241 A1 | 7/2010 | McCormack et al. |
| 2010/0211075 A1 | 8/2010 | Stone |
| 2010/0241121 A1 | 9/2010 | Logan et al. |
| 2010/0249786 A1 | 9/2010 | Schmieding et al. |
| 2010/0268275 A1 | 10/2010 | Stone et al. |
| 2010/0292732 A1 | 11/2010 | Hirotsuka et al. |
| 2010/0292792 A1 | 11/2010 | Stone et al. |
| 2010/0305709 A1 | 12/2010 | Metzger et al. |
| 2011/0015674 A1 | 1/2011 | Howard et al. |
| 2011/0015675 A1 | 1/2011 | Howard et al. |
| 2011/0022083 A1 | 1/2011 | DiMatteo et al. |
| 2011/0054526 A1 | 3/2011 | Stone et al. |
| 2011/0087247 A1 | 4/2011 | Fung et al. |
| 2011/0087280 A1 | 4/2011 | Albertorio |
| 2011/0087284 A1 | 4/2011 | Stone et al. |
| 2011/0098727 A1 | 4/2011 | Kaiser et al. |
| 2011/0106089 A1 | 5/2011 | Brunnett et al. |
| 2011/0106153 A1 | 5/2011 | Stone et al. |
| 2011/0125189 A1 | 5/2011 | Stoll, Jr. et al. |
| 2011/0160767 A1 | 6/2011 | Stone et al. |
| 2011/0160768 A1 | 6/2011 | Stone et al. |
| 2011/0184516 A1 | 7/2011 | Baird et al. |
| 2011/0208194 A1 | 8/2011 | Steiner et al. |
| 2011/0208239 A1 | 8/2011 | Stone et al. |
| 2011/0208240 A1 | 8/2011 | Stone et al. |
| 2011/0213416 A1 | 9/2011 | Kaiser |
| 2011/0213417 A1 | 9/2011 | Foerster et al. |
| 2011/0218538 A1 | 9/2011 | Sherman et al. |
| 2011/0218625 A1 | 9/2011 | Berelsman et al. |
| 2011/0224799 A1 | 9/2011 | Stone |
| 2011/0264140 A1 | 10/2011 | Lizardi et al. |
| 2011/0264141 A1 | 10/2011 | Denham et al. |
| 2011/0270278 A1 | 11/2011 | Overes et al. |
| 2011/0270293 A1 | 11/2011 | Malla et al. |
| 2011/0270306 A1 | 11/2011 | Denham et al. |
| 2011/0295279 A1 | 12/2011 | Stone et al. |
| 2011/0301708 A1 | 12/2011 | Stone et al. |
| 2011/0319896 A1 | 12/2011 | Papenfuss et al. |
| 2012/0004672 A1 | 1/2012 | Giap et al. |
| 2012/0041485 A1 | 2/2012 | Kaiser et al. |
| 2012/0041486 A1 | 2/2012 | Stone et al. |
| 2012/0046693 A1* | 2/2012 | Denham ............ A61B 17/0401 606/232 |
| 2012/0053630 A1 | 3/2012 | Denham et al. |
| 2012/0053641 A1 | 3/2012 | Meridew |
| 2012/0059417 A1 | 3/2012 | Norton et al. |
| 2012/0059418 A1 | 3/2012 | Denham et al. |
| 2012/0071976 A1 | 3/2012 | May et al. |
| 2012/0089193 A1 | 4/2012 | Stone et al. |
| 2012/0095470 A1 | 4/2012 | Kaiser et al. |
| 2012/0095556 A1 | 4/2012 | Re et al. |
| 2012/0109142 A1 | 5/2012 | Dayan |
| 2012/0109156 A1 | 5/2012 | Overes et al. |
| 2012/0109194 A1 | 5/2012 | Miller et al. |
| 2012/0116452 A1 | 5/2012 | Stone et al. |
| 2012/0130424 A1 | 5/2012 | Sengun et al. |
| 2012/0150297 A1 | 6/2012 | Denham et al. |
| 2012/0150301 A1 | 6/2012 | Gamache et al. |
| 2012/0165866 A1 | 6/2012 | Kaiser et al. |
| 2012/0165867 A1 | 6/2012 | Denham et al. |
| 2012/0165938 A1 | 6/2012 | Denham et al. |
| 2012/0172986 A1 | 7/2012 | Stone et al. |
| 2012/0179254 A1 | 7/2012 | Saliman |
| 2012/0180291 A1 | 7/2012 | Oren et al. |
| 2012/0197271 A1 | 8/2012 | Astorino et al. |
| 2012/0203288 A1 | 8/2012 | Lange et al. |
| 2012/0239086 A1 | 9/2012 | Reznik et al. |
| 2012/0245585 A1 | 9/2012 | Kaiser et al. |
| 2012/0253355 A1 | 10/2012 | Murray et al. |
| 2012/0290002 A1 | 11/2012 | Astorino |
| 2012/0290004 A1 | 11/2012 | Lombardo et al. |
| 2012/0290006 A1 | 11/2012 | Collins et al. |
| 2012/0296345 A1 | 11/2012 | Wack et al. |
| 2012/0296427 A1 | 11/2012 | Conner et al. |
| 2012/0303046 A1 | 11/2012 | Stone et al. |
| 2013/0012962 A1 | 1/2013 | Stone |
| 2013/0018416 A1 | 1/2013 | Lombardo et al. |
| 2013/0023928 A1 | 1/2013 | Dreyfuss |
| 2013/0023929 A1 | 1/2013 | Sullivan et al. |
| 2013/0023930 A1 | 1/2013 | Stone et al. |
| 2013/0035698 A1 | 2/2013 | Stone et al. |
| 2013/0046341 A1 | 2/2013 | Stone et al. |
| 2013/0072989 A1 | 3/2013 | Overes et al. |
| 2013/0096611 A1 | 4/2013 | Sullivan |
| 2013/0096612 A1 | 4/2013 | Zajac et al. |
| 2013/0110165 A1 | 5/2013 | Burkhart et al. |
| 2013/0131722 A1 | 5/2013 | Marchand et al. |
| 2013/0158601 A1 | 6/2013 | Stone et al. |
| 2013/0165972 A1 | 6/2013 | Sullivan |
| 2013/0178898 A1 | 7/2013 | Arnett et al. |
| 2013/0190818 A1 | 7/2013 | Norton |
| 2013/0190819 A1 | 7/2013 | Norton |
| 2013/0237997 A1 | 9/2013 | Arai et al. |
| 2013/0296893 A1 | 11/2013 | Dean et al. |
| 2013/0296931 A1 | 11/2013 | Sengun |
| 2013/0317544 A1 | 11/2013 | Ferguson et al. |
| 2013/0325063 A1 | 12/2013 | Norton et al. |
| 2013/0345749 A1 | 12/2013 | Sullivan et al. |
| 2014/0039503 A1 | 2/2014 | Pilgeram |
| 2014/0081322 A1* | 3/2014 | Sengun ............ A61B 17/0401 606/228 |
| 2014/0135835 A1 | 5/2014 | Stone et al. |
| 2014/0163679 A1 | 6/2014 | Re et al. |
| 2014/0188163 A1 | 7/2014 | Sengun |
| 2014/0257382 A1 | 9/2014 | McCartney |

FOREIGN PATENT DOCUMENTS

| | | |
|---|---|---|
| DE | 4243715 A1 | 7/1994 |
| DE | 19503504 A1 | 3/1996 |
| EP | 153831 A2 | 9/1985 |
| EP | 253526 A1 | 1/1988 |
| EP | 0440371 A1 | 8/1991 |
| EP | 0611551 A1 | 8/1994 |
| EP | 1155776 A2 | 11/2001 |
| EP | 1369089 A2 | 12/2003 |
| EP | 2544607 A1 | 1/2013 |
| EP | 2548519 A2 | 1/2013 |
| EP | 2596755 A2 | 5/2013 |
| EP | 2662030 A1 | 11/2013 |
| EP | 2662032 A1 | 11/2013 |
| FR | 1166884 A | 11/1958 |
| FR | 2606996 A1 | 5/1988 |
| FR | 2676638 A1 | 11/1992 |
| GB | 2093353 A | 9/1982 |
| WO | 9511631 A1 | 5/1995 |
| WO | 00/44291 A1 | 8/2000 |
| WO | 0128457 A1 | 4/2001 |
| WO | 03007861 A1 | 1/2003 |
| WO | 2007/010389 A1 | 1/2007 |
| WO | 2008128075 A1 | 10/2008 |
| WO | 2009105880 A1 | 9/2009 |
| WO | 2011112371 A1 | 9/2011 |
| WO | 2012134999 A1 | 10/2012 |
| WO | 2012158583 A1 | 11/2012 |
| WO | 2013006820 A1 | 1/2013 |

OTHER PUBLICATIONS

U.S. Appl. No. 13/792,982, filed Mar. 11, 2013.
Australian Examination Report for Application No. 2013202699 dated Feb. 21, 2014.
Extended European Search Report for Application No. EP 12164104 dated Jul. 11. 2012.
BIOMET Sports Medicine: Micromax Flex Suture Anchor, (2008).
Burkinshaw, U.S. Appl. No. 60/418,545, filed Oct. 15, 2002.
Chen et al., Journal of Orthopaedic Research, pp. 1432-1438, Nov. 2009.
Chen et al., Poster No. 538, 54th Annual Meeting of the Orthopaedic Research Society, San Francisco, CA Mar. 2008.

(56) References Cited

OTHER PUBLICATIONS

Cole et al., American Journal of Sports Medicine, vol. XX, No. X, 2011.
Conmed: Linvatec: Shoulder Restoration System Y-Knot 1.3mm All Suture Anchor, © 2011 Linvatec Corporation, a subsidiary of ConMed Corporation—CBR 3057 (4 pages).
European Search Report, EP 10173568, dated Nov. 30, 2010.
HHS Tube, Fort Wayne Metals Research Products Corp., 2009.
International Search Report PCT/US2010/042264, dated Sep. 30, 2010.
Medtronic, The VISAO High-Speed Otologic Drill Catalog, 2007.
Perthes, German Surgery Periodical, vol. 85, Commermorative Publication, pp. 2-18, 1906.
Perthes, Ober Operationen bel habitueller Schulterluxaton, X, pp. 199-227, 85.
Sugaya et al., Journal of Bone and Joint Surgery, vol. 85-A, No. 5, pp. 878-884, May 2003.
U.S. Appl. No. 13/368,730, filed Feb. 8, 2012.
U.S. Appl. No. 13/588,592, filed Aug. 17, 2012.
U.S. Appl. No. 13/783,804, filed Mar. 4, 2013.
U.S. Appl. No. 61/679,336, filed Aug. 3, 2012.
U.S. Appl. No. 13/085,882, filed Apr. 13, 2011.
U.S. Appl. No. 13/588,586, filed Aug. 17, 2012.
U.S. Appl. No. 13/303,849, filed Nov. 23, 2011.
Extended European Search Report for Application No. EP14157877 dated Jul. 4, 2016.

\* cited by examiner

FILAMENTARY FIXATION DEVICE AND ASSEMBLY AND METHOD OF ASSEMBLY, MANUFACTURE AND USE

BACKGROUND OF THE INVENTION

Suture anchors are devices useful for fixing damaged soft tissue, such as tendons and ligaments, to bone. Presently, certain of these devices may be secured to bone either through a solid-body anchor having threaded mechanism or interference fit. Generally, these devices are constructed from metal, polymer, or bioresorbable material. Consequently, these suture anchor devices tend to be rigid structures that require a minimum amount of material to provide the strength needed to prevent catastrophic failure. This minimum amount of material dictates the volume of bone that must be removed for implantation to occur, which may be significant.

Further, current suture anchors typically include an eyelet at one end containing the suture designated for anchoring. This configuration commonly requires the suture anchor to be inserted into bone first, at which point the suture is passed through the target tissue where it is tensioned and tied-off with a surgical knot. Unfortunately, these knots may loosen or come undone compromising the procedure. Additionally, setting the proper tension may prove difficult as the operator may not be aware of the final tension of the suture until the surgical knot is set.

Thus, there is a need for an all filament anchor that provides for less bone removal during pilot hole creation without compromising pullout strength and provides flexibility in setting the optimum suture tension without the need for a complex surgical knot.

BRIEF SUMMARY OF THE INVENTION

Generally, the present invention includes devices, assemblies, systems, kits and methods of manufacture, assembly and use for the repair of soft tissue. Specifically, in one embodiment, the present invention includes a filamentary fixation device having a filamentary sleeve, loading member, and retriever member. In another embodiment of the present invention, the filamentary fixation device may have the filamentary sleeve, loading member, and a working suture. The filamentary fixation device can be used to anchor damaged soft tissue to bone.

According to a first embodiment of the present invention, a method of assembling a filamentary fixation assembly, including obtaining a filamentary sleeve having a pathway therethrough, a loading member positioned through at least a portion of the pathway, and a retriever member positioned through at least a portion of the pathway. The method also includes engaging a working suture with the retriever member. Additionally, the method includes positioning at least a portion of the working suture in the pathway using the retriever member. Further included in the method is the step of engaging the working suture with the loading member.

Further, the positioning step may include tensioning the retriever member such that at least a portion of the working suture may be disposed within the pathway and the working tails may pass through the pathway. Additionally, the step of engaging the working suture with the loading member may include tying the working tails into a sliding knot around the loading member. Further, the method may thus include the additional step of tensioning the loading member such that the sliding knot passes into the pathway.

Continuing with this embodiment, the retriever member may include a first end and a second end with the first end including a first loop configuration. The loading member may also include a first end and a second end, with the first end including a second loop configuration. Further, the filamentary sleeve may include a first end and a second end. The retriever member may be positioned through the pathway of the filamentary sleeve such that the first loop configuration may extend from the first end of the filamentary sleeve and the second end may extend from the second end of the filamentary sleeve. Similarly, the loading member may be positioned through the pathway of the filamentary sleeve such that the second loop configuration may extend from the second end of the filamentary sleeve and the first end may extend from the first end of the filamentary sleeve. As such, the engaging the retriever member with the working suture may include passing the working tails through the loop configuration. Further, the step of positioning at least a portion of the working suture in the pathway using the retriever member can include tensioning of the retriever member by pulling on the second end of the retriever member to pull the working suture into the pathway. Additionally, the aforementioned tying step may include tying the working tails through the second loop configuration of the loading member. Further, tensioning of the loading member may include pulling the second end of the loading member to pull the sliding knot into the pathway.

In another embodiment of the present invention, a filamentary fixation assembly includes a filamentary sleeve constructed entirely of filamentary material and having a pathway extending therethrough. Further included in the assembly is a loading member, which includes a first loop and at least one loading tail that is at least partially disposed within the pathway. Additionally, a working suture, which includes at least a first working tail, is included in the assembly.

The assembly can further include a retriever member. The retriever member may be at least partially disposed within the pathway and include a second loop and at least one retriever tail. The second loop may be positioned opposite the first loop, and the at least one retriever tail may be positioned adjacent the first loop.

Further, the loading member may be constructed from a single line of filament. Further, the first loop may be formed by folding the single line of filament along its length, and the at least one loading tail may be two loading tails. Alternatively, the first loop may be a pre-formed loop, and the at least one loading tail may extend from the first loop.

Moreover, the retriever member may be constructed from a single line of filament. Further, the second loop may be formed by folding the single line of filament along its length, and the at least one retriever tail may be two retriever tails. Alternatively, the second loop may be a pre-formed loop, and the at least one retriever tail may extend from the second loop. Optionally, the retriever member may be constructed from memory metal. In another alternative, the filamentary sleeve may have a sidewall defined by the pathway, the sidewall having a plurality of pass-throughs disposed along one side of the filamentary sleeve.

In a further embodiment of the present invention, a method of anchoring tissue to bone using a filamentary sleeve is disclosed herein. The filamentary sleeve includes a pathway therethrough and a retriever member and loading member at least partially disposed within the pathway. The method includes engaging the retriever member with working tails of a working suture connected to the tissue, tensioning the retriever member such that at least a portion of the working suture is disposed within the pathway and the working tails pass through the pathway, inserting the filamentary sleeve into a bore hole in bone such that the loading member and working suture extend from the bore hole, tying the working tails into a sliding knot around the loading member and tensioning the loading member such that the sliding knot passes into the pathway, thereby fixedly securing the filamentary sleeve within the bore hole.

Optionally, the sliding knot may be a half-hitch knot. Further, the step inserting of the sleeve into the bore hole may occur prior to the tying step. Optionally, the step inserting of the sleeve into the bore hole may occur prior to the step of engaging the retriever member with the working tails.

Continuing with this embodiment, the method may further include the step of pulling on either or both the loading member and working suture to deploy the filamentary sleeve within the bore hole. Additionally, the filamentary sleeve can be constructed entirely of filamentary material and includes a sidewall defined by the pathway. The sidewall may optionally include a plurality of pass-throughs disposed along one side of the filamentary sleeve.

Continuing with this embodiment, the retriever member may include a first end and a second end. The first end may include a first loop configuration. The loading member may also include a first end and a second end where this first end may have a second loop configuration. Also, the filamentary sleeve may include a first end and a second end. The retriever member may be positioned through the pathway of the filamentary sleeve such that the first loop configuration extends from the first end of the filamentary sleeve and the second end may extend from the second end of the filamentary sleeve. Also, the loading member may be positioned through the pathway of the filamentary sleeve such that the second loop configuration may extend from the second end of the filamentary sleeve and the first end may extend from the first end of the filamentary sleeve.

Further, the step of engaging may include passing the working tails through the loop configuration, and the step of tensioning of the retriever member may include pulling on the second end of the retriever member to pull the working suture into the pathway.

Moreover, continuing with this embodiment, the step of tying may include tying the working tails through the second loop configuration of the loading member, and the step of tensioning of the loading member may include pulling the second end of the loading member to pull the sliding knot into the pathway.

BRIEF DESCRIPTION OF THE DRAWINGS

These and other features, aspects, and advantages of the present invention will become better understood with regard to the following description, appended claims, and accompanying drawings where:

DETAILED DESCRIPTION

Figure 1A:
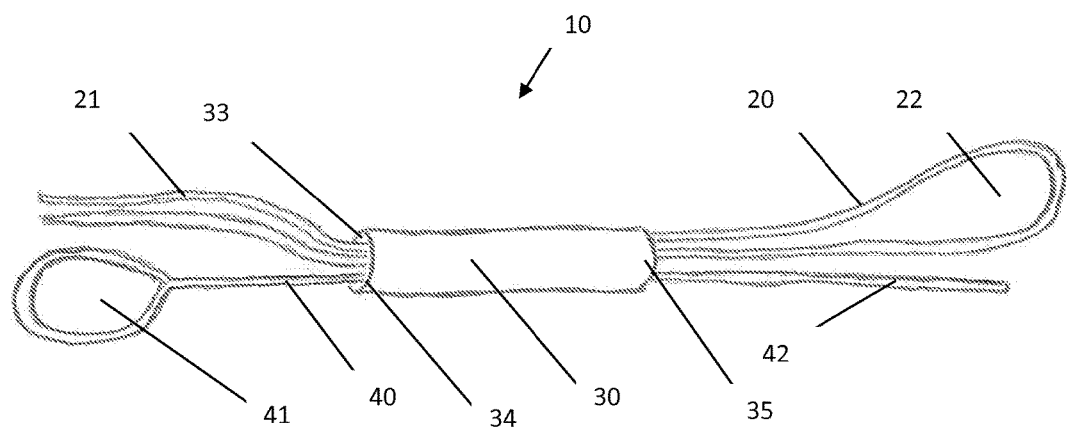
FIG. 1A shows a perspective view of an embodiment of a filamentary fixation device having a first embodiment of a filamentary sleeve.

FIG. 1A depicts an embodiment of a filamentary fixation assembly 10, which includes a filamentary sleeve 30, a retriever member 40, and a loading member 20. The filamentary sleeve 30 may be cylindrical in shape and include a pathway 33 extending therethrough and a wall thickness 36 defined between the pathway 33 and an outer surface of the sleeve 30.

Figure 1B:
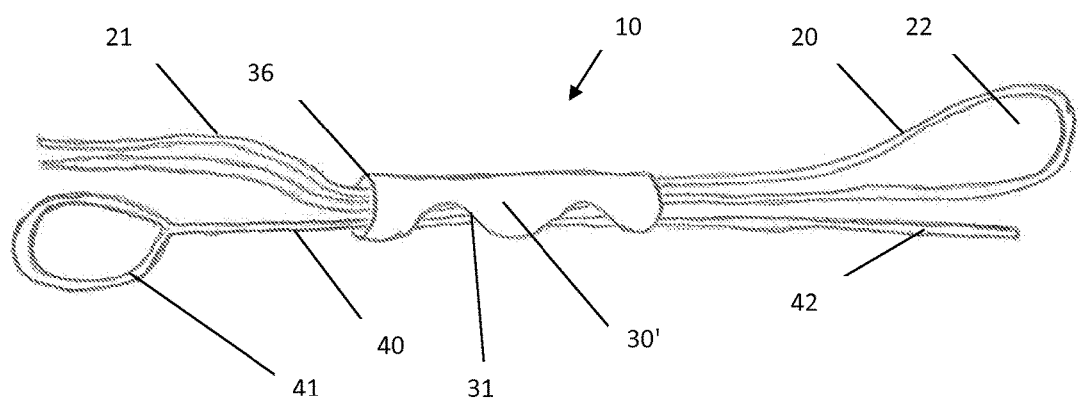
FIG. 1B shows a perspective view of the filamentary fixation device of FIG. 1A having a second embodiment of the filamentary sleeve.

In a substitute embodiment of the filamentary sleeve 30, the filamentary sleeve 30 may be provided with an alternative configuration as illustrated in FIG. 1B. In such embodiment, the filamentary sleeve 30' may be generally cylindrical with a plurality of pass-throughs 31. A set of these pass-throughs 31 may provide filamentary material positioned within pathway 33, such as retriever member 40, loading member 20, and working suture 50, to instead have an alternative configuration relative to sleeve 30'. For example, the filamentary material (e.g., member 40, member 20, suture 50) extends through a portion of the pathway, exits the pathway 33 by traversing wall thickness 36 at a pass-through 31, where it travels externally along a portion of the length of the filamentary sleeve 30', then re-enters the pathway 33 at another pass-through 31 where it continues through another portion of the pathway 33. These pass-throughs 31 may be symmetrically disposed along one side of the filamentary sleeve 30'. The symmetrical arrangement is such that when the filamentary sleeve 30' is folded in half at least one pass-through 31 will face an opposing pass-through 31. These pass-throughs 31 may also facilitate folding and compressing of the filamentary sleeve 30' by drawing together discrete portions of the filamentary sleeve that are disposed between the pass-throughs as the filamentary material disposed within and through the pass-throughs are tensioned.). Moreover, such pass-throughs may result in greater fixation strength with a bore hole to be prepared in the bone (if used in this manner, as described further below). Further, these pass-throughs 31 may facilitate a solid anchoring position where the filamentary sleeve 30' is folded and inserted into a bore hole 81 in bone 80. As such, a pulling force, typically originating from the filamentary material passing through the filamentary sleeve 30', creates a deploying friction between the filamentary sleeve 30' and bore hole 81 (if present, as in FIGS. 4 and 5). This friction buckles the filamentary sleeve 30' material between the pass-throughs 30' causing them to expand outwardly against the bore hole 81, thereby significantly increasing the friction against the bone, which provides for a very strong anchor. In one example, the filamentary sleeve 31' can be the Iconix® all suture anchor system (Howmedica Osteonics, Mahwah, N.J.). Additional example are disclosed in U.S. Provisional Application No. 61/679,336, filed Aug. 3, 2012, U.S. application Ser. No. 13/303,849, filed Nov. 23, 2011, Ser. No. 13/588,586, filed Aug. 17, 2012, and Ser. No. 13/588,592, filed Aug. 17, 2012, and U.S. Pat. Nos. 5,989,252 and 6,511,498, the entireties of which are incorporated by reference herein as if fully set forth herein and all of which are assigned to the same entity as the present application. As described in certain of these references, the pass-throughs can alternatively be positioned elsewhere on the sleeve such that they may or may not be symmetrical. Moreover, in another alternative, the sleeve could include a set of pass-throughs in the middle of the sleeve, along or in addition to one or more other sets of pass-throughs. Such a set of pass-through in the middle of the sleeve could also make folding the sleeve over an insertion instrument (not shown) easier, and thus also result in a more condensed structure on such an instrument, which thereby could necessitate a smaller bore hole in bone. While any of these sleeves (including sleeves 30 and 30') could be used in the present invention, sleeve 30 is illustrated throughout the various disclosed embodiments for reasons of clarity and simplicity.

In one embodiment of the retriever member 40, the retriever member 40 may include a retriever loop 41 that is a pre-formed loop and one retriever tail 42 extending therefrom, as illustrated in FIGS. 1A and 1B. Alternatively, the retriever member 40 could have a plurality of retriever tails (not shown) extending from the retriever loop 41. In one such configuration, the retriever member 40 may be constructed from a single line of filament wherein the retriever loop 41 and tail 42 are formed by a locking Brummel splice, as is known in the art. However, the locking Brummel splice is merely an example of the various approaches known in the art for forming a retriever loop 41 and a single retriever tail 42 or a plurality of retriever tails (not shown) extending therefrom. Another example of the above mentioned configuration is a suture shuttle constructed from memory metal materials, such as nitinol, an example of which is disclosed in U.S. Provisional Application No. 61/755,654, filed Jan. 1, 2013 the entirety of which is incorporated by reference herein as if fully set forth herein and which is assigned to the same entity as the present application. Other alternative examples are illustrated in the above applications incorporated by reference, specifically the '336, '586 and '592 applications.

In an alternative embodiment of the retriever member 40 the retriever member 40 may be a single line of filament (not shown). In such an embodiment, the single line of filament may be folded along its length forming a retriever loop and a pair of retriever tails (not shown). An example of such an alternative is illustrated in U.S. application Ser. No. 13/783,804, filed Mar. 4, 2013, the entirety of which is incorporated by reference herein as if fully set forth herein and which is assigned to the same entity as the present application.

The loading member 20 may be similarly configured to that of the retriever member 40, and thus may have any of the above arrangements as described above as to the retriever member 40. In one embodiment, as illustrated in FIGS. 1A and 1B, the loading member 20 may be constructed from a single line of filament that may be folded along its length to form a loading loop 22 and a pair of loading tails 21.

In an alternate embodiment (not shown), the loading member 20 may include a loading loop that is a pre-formed loop and one loading tail, or a plurality of loading tails, extending from the loading loop. In one such configuration, the loading member 20 may be constructed from a single line of filament wherein the loading loop and tail are formed by a locking Brummel splice, as is known in the art. However, the locking Brummel splice configuration is merely an example of the various approaches known in the art for forming a single loop with a tail extending therefrom, any of which may be utilized. Thus, while FIGS. 1A and 1B (and throughout FIGS. 2-8) illustrate a preferred embodiment of both the loading loop 20 and retriever member 40, they may instead be present in a variety of other configurations, and may have similar or different configurations from one another as desired.

Continuing with the embodiment of the filamentary fixation assembly 10 as illustrated in FIG. 1A, the retriever member 20 may be partially disposed within a pathway 33 of the filamentary sleeve 30 such that the retriever loop 41 extends out of one side 34 of the filamentary sleeve 30 and the retriever tail 42 extends from the from the other side 35 of the filamentary sleeve 30. The loading loop 40 may also be partially disposed within the pathway 33 such that the loading loop 22 extends out of one side 35 of the filamentary sleeve 30 and the loading tails 21 extend out of the other side 34. Generally, the loading loop 22 is positioned on the opposite side 35 of filamentary sleeve 30 as the retriever loop 41, but on the same side 35 and adjacent to the retriever tail 42.

Figure 3:
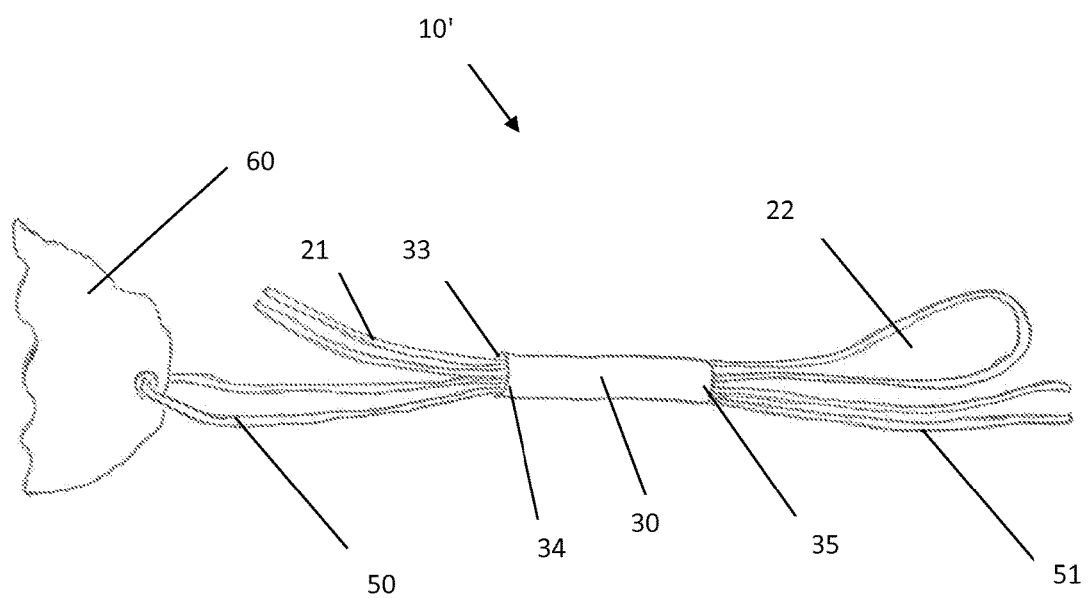

FIG. 3 depicts another embodiment of the filamentary fixation assembly 10', which may include the filamentary sleeve 30, the loading member 20, and a working suture 50. The filamentary sleeve 30 and loading member 20 may be of any of the embodiments and configurations as described in the above embodiment of the filamentary fixation assembly 10.

In one embodiment of the working suture 50, the working suture may be constructed from a single line of filament that may be folded along its length to form a pair of working tails 51.

In an alternate embodiment of the working suture 50, the working suture 50 may include a pre-formed loop and at least one working tail extending from the pre-formed loop (not shown). In one such configuration, the working suture 50 may be constructed from a single line of filament wherein the pre-formed loop and working tail are formed by a locking Brummel splice, as is known in the art. However, the locking Brummel splice configuration is merely an example of the various approaches known in the art for forming a single loop with a tail extending therefrom, any of which may be utilized. An example of such a working suture can be found in the above, incorporated by reference, '804 application, as well as U.S. application Ser. No. 13/441,290, filed Apr. 6, 2012, the entirety of which is incorporated by reference herein as if fully set forth herein and which is assigned to the same entity as the present application. Such working sutures may be secured to the tissue 60 by, for example, passing a free end around or through the tissue, and then through the pre-formed loop. The free end may then be tensioned to pull the loop against the tissue, similar to a "luggage tag" configuration.

As has been described in the prior embodiment of the filamentary fixation assembly 10, the loading member 20 is partially disposed within the pathway 33 of the filamentary sleeve 30 such that the loading loop 22 extends out of one side 35 of the filamentary sleeve 30 and the loading tails 21 extend from the other side 34. The working suture 50 also may be partially disposed within the pathway 33 such that the working tails 51 extend from the filamentary sleeve 30 on the same side 35 as and adjacent to the loading loop 22. In some embodiments, the working tails 51 may be tied around the loading loop 22 in a sliding knot configuration, such as a half-hitch knot, as discussed further below.

As will be described in greater detail below, assembly 10' can be assembled from assembly 10 using retriever member 40, or a similar device suitable to pass the tails 51 of working suture 50 through sleeve 30.

The filamentary sleeve 30, retriever member 40, loading member 20 and working suture 50 may be constructed from filamentary material, such as homogenous or heterogeneous materials including, but not limited to, polyester, polyethylene (including ultra-high molecular weight polyethylene (UHMWPE)), polytetrafluorethylene (including expanded polytetrafluorethylene), nylon, polypropylene, aramids (such as Kevlar-based materials), polydioxanone, polygycolic acid, and organic material (silk, animal tendon, or the like). Further, the retriever member 40 may be constructed from memory metal material such as nitinol, and the filamentary sleeve 30 may be entirely constructed from filamentary material. Therefore, the filamentary fixation device 10, 10' may be, and is preferably, constructed entirely from filamentary material.

The filamentary fixation device 10, 10' may be provided to the user in any number of arrangements. In one arrangement, the end user may be provided the embodiment of the filamentary fixation assembly 10 that includes the loading member 20 and retriever member 40 disposed within the pathway 33 of the filamentary sleeve 30. However, in another arrangement, the user may be provided this embodiment of the filamentary fixation device 10 along with the working suture 50 disassembled from the filamentary fixation device 10. In such a circumstance, the user may convert this embodiment into the other embodiment of the filamentary fixation device 10' that includes the loading loop 20 and working suture 50 disposed within the pathway 33 of the filamentary sleeve 30. However, in another arrangement, the user may only be provided the filamentary fixation assembly 10'.

In another arrangement, a kit may be provided with a filamentary sleeve 30, loading member 20, retriever member 40, and working suture 50 either in assembled form or unassembled leaving it to the user to arrange the device as he or she desires for a particular application. If the device comes to the user unassembled, the kit may further include a suture passing device, such as any of the variations of retriever member 40 and loading member 20 described above. Preferably, if included, such a suture passer would be manufactured from metal wire to provide adequate rigidity in passing the various filaments through the sleeve 30. Alternatively, the working suture 50, retriever member, and/or loading member may be provided affixed to a needle (not shown) to provide the adequate rigidity for passing through sleeve 30. Any kit of the present invention may include a plurality of any or all of the sleeve 30, member 20, member 40 and/or suture 50.

The present invention also includes a method of assembly of one embodiment of the filamentary fixation device 10, including a filamentary sleeve 30, loading member 20, and retriever member 40, is now described. In this embodiment, the filamentary sleeve 30, retriever member 40, and loading member 20 may be obtained unassembled and preferably constructed from filamentary material. The loading member 20 is positioned into the pathway 33 of the filamentary sleeve 30 such that the loading loop 22 and loading tails 21 extend from the filamentary sleeve 30 at opposing sides as shown in FIG. 1. The retriever member 40 may then be positioned within the pathway 33 such that the retriever loop 41 extends from the same side 34 of the filamentary sleeve 30 as that of the loading tails 21, and the retriever tail 42 extends from the same side 35 as the loading loop 22. While the loading member 20 is described herein as being positioned within the pathway 33 prior to the retriever member 40, the retriever member 40 may be positioned within the pathway 33 first. It is envisioned that a method may also entail the use of a suture passer, as described above.

Figure 5:
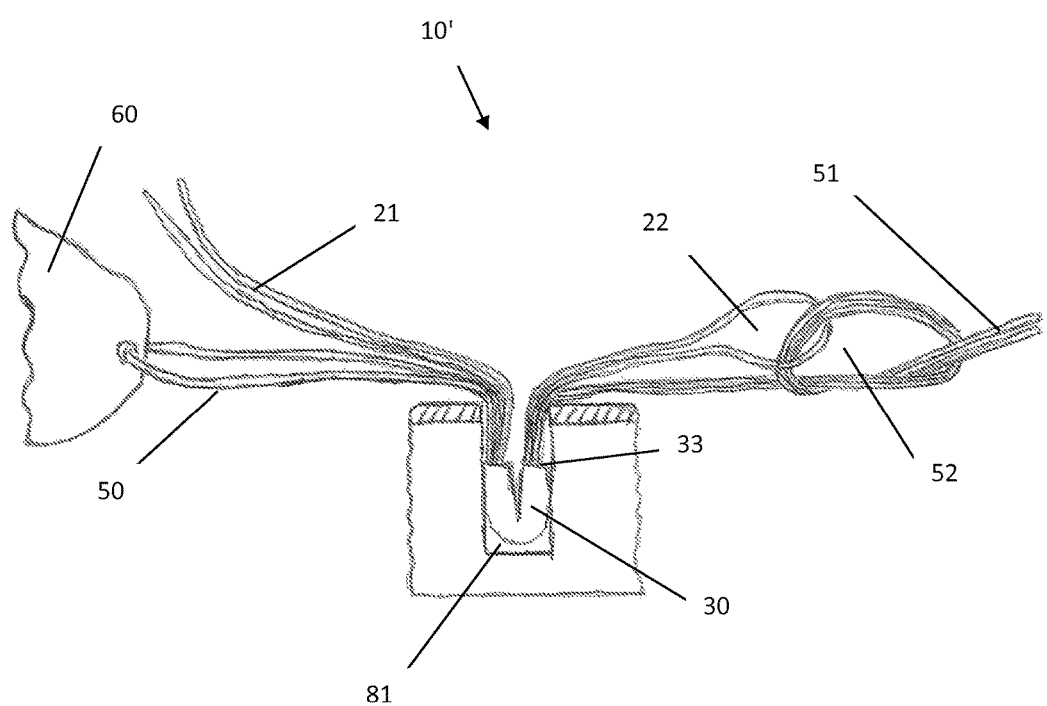

In another embodiment of the filamentary fixation device 10', the working suture 50 and filamentary sleeve 30 may be obtained, wherein the filamentary sleeve 30 includes the loading member 20 and retriever member 40 disposed within the pathway 33 of the filamentary sleeve 30, such that the loading loop 20 and retriever tails 42 extend from one side of the filamentary sleeve 30 and the retriever loop 41 and loading tails 21 extend from the other. The working suture 50 may be placed into an engagement configuration with the retriever member 40. This engagement configuration could include simply passing the working tails 42 through the retriever loop 41 or tying the working tails 42 to the retriever loop 41. The retriever member 40 is then tensioned at the retriever tail 42 such that a portion of the working suture 50 enters into the pathway 33 of filamentary sleeve 30, and preferably such that the working tails 51 extend from the same side 35 of the filamentary sleeve 30 as the loading loop 22. The working tails 51 may then be tied to the loading loop 22 in a sliding knot configuration, preferably a half-hitch knot 52, as shown in FIG. 5. Tension may then be applied to the working tails 51 and a working loop 52 located opposite the working tails 51 in an opposite direction. Simultaneously, tension may be applied to the loading tails 21 such that the half-hitch knot 52 enters into the pathway 33 of the filamentary sleeve 30. In this fashion, the working suture 50 may be fixedly secured to the sleeve 30.

The filamentary fixation assembly 10, 10' may be used in soft tissue repair procedures to fix soft tissue to bone as illustrated in FIGS. 2-8, for example. Such soft tissue repair can be performed in any soft tissue, include such tissue in the foot, ankle, hand, wrist, elbow, hip and shoulder, and in particular soft tissue repair of the rotator cuff and labrum in the hip and shoulder. FIGS. 2-8 illustrate one embodiment of such a method of repair, as performed specifically in the reattachment of the labrum to the glenoid, though this method may be useful and be performed in other soft tissues of the body.

Figure 2:
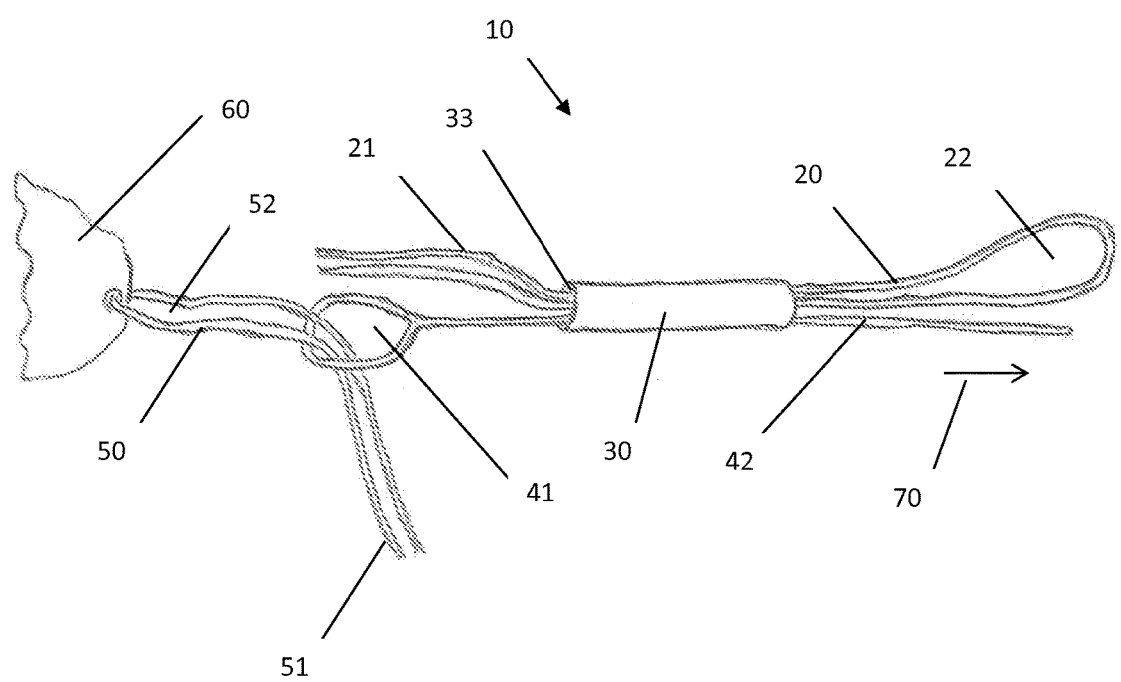
FIGS. 2-8 show subsequent steps of an exemplary method of use and assembly illustrated using the filamentary fixation device of FIG. 1A.

Initially in this embodiment, as illustrated in FIG. 2, the working suture 50 may be passed around or through the tissue designated for repair. Where the working suture 50 is a single line of filament, one end of the filament may be passed through the tissue 60, as seen in FIG. 2, using a suture passer, as is known in the art, or other techniques that are known in the art. In other instances, the single line of filament many be folded along its length forming a looped-end 52 and a pair of working tails 51, in which case the looped-end 52 is passed through the tissue and the working tails 51 are passed through the looped-end 52 around a portion of the tissue in a "luggage-tag" configuration (not shown). This "luggage-tag" configuration may also be utilized where the working suture 50 includes the pre-formed loop and single working tail extending from the pre-formed loop as described above, or where the working suture 50 is provided pre-assembled with the filamentary sleeve 30, also described above, in which case the entire filamentary fixation assembly 10' would be passed through the looped end (not shown). It is noted that where the working suture 50 is provided already assembled to the filamentary sleeve 30 in conjunction with the loading loop 20, the following steps utilizing the retriever loop 40 may be skipped.

Continuing with this embodiment, and with reference to FIG. 2, the filamentary fixation assembly 10 may be introduced to the surgical repair site where the working tails 51 engage the retriever loop 41 of the retriever member 40. This engagement can be as simple as threading the working tails 51 through the retriever loop 41. The retriever member 40 is then tensioned at the retriever tail 42 as demonstrated by arrow 30. This tension passes the retriever loop 41 through the pathway 33 of the filamentary sleeve such that the working suture 50 is partially disposed within the filamentary sleeve 30 and the working tails extend from the pathway 33 and reside adjacent the loading loop 22, as shown in FIG. 3.

Figure 4A:
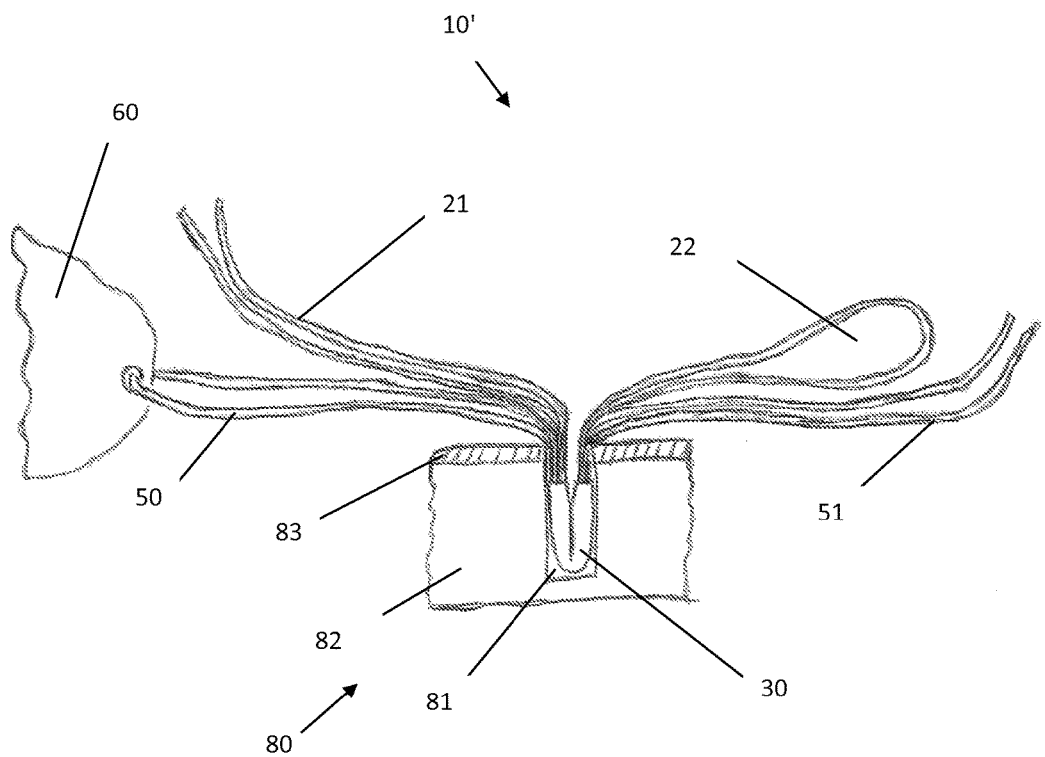
Figure 4B:
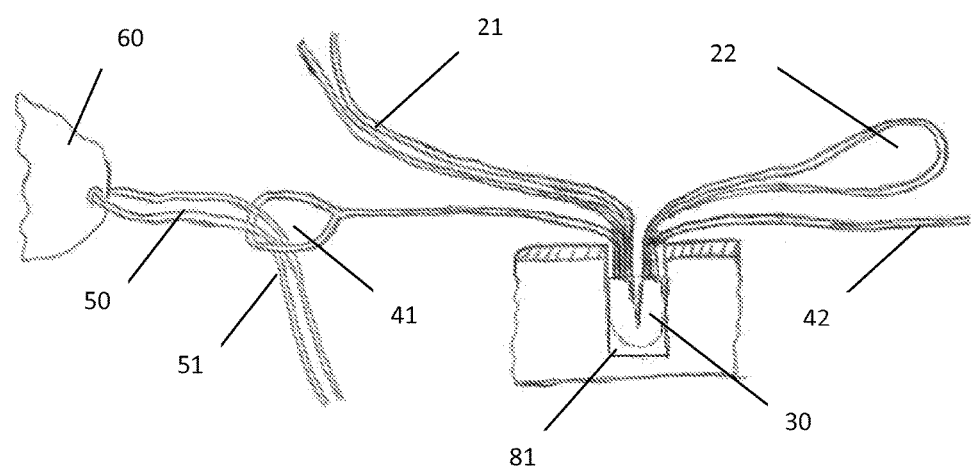

With the loading member 20 and working suture 50 now disposed within the filamentary sleeve 30 as shown in FIG. 3, the filamentary sleeve 30 may be folded and inserted into a bore hole 81 that has been formed in bone 80 such that both ends of the loading member 20 and working suture 50 extend from the bore hole 81 as shown in FIG. 4A. The bore hole 81 is generally formed in cancellous bone 82 through cortical bone 83, and the filamentary sleeve 30 is generally inserted into the cancellous region of the bore hole 81, as shown. Once the filamentary sleeve 30 is inserted in the bore hole 81, either or both the loading member 20 and working suture 50 may be tensioned to deploy sleeve 30 and firmly seat the sleeve 30 within the bore hole 81. Such deployment is described in many of the above-incorporated applications. Due to the relatively thin nature of the filamentary sleeve 30 and filamentary material located therein, the bore hole 81 may generally be very small as compared to the bore hole 81 necessary to accommodate a current rigid suture anchor, thereby preserving native bone. For example, the sleeve 30 may be constructed of #5 suture, and working suture 50 and loading member 20 may both be constructed of #2 suture. Thus, in a preferred embodiment, bore hole 81 may have a diameter of about 2.3 mm.

While the engagement of the working tails 51 to the retriever loop 41 is described as occurring prior to folding and inserting the filamentary sleeve 30 into the bore hole 81, this is merely an illustrative order of performance, and indeed, has been presented in this manner for the sake of clarity of illustration. In a preferred embodiment, the filamentary sleeve 30 may be folded and inserted into the bore hole 81 prior to engaging the working tails 51 with the retriever loop 41. As such, the configuration as in FIG. 4B would instead be achieved by first inserting and deploying sleeve 30 in bore hole 81, followed by passing the tails 51 through retriever loop 41. Then, in such an alternative, the working tails would be passed through the pathway 33, as detailed above, while the filamentary sleeve 30 is folded and deployed within the bore hole 81.

Referring to FIG. 5, the working tails 51 are then engaged with loading loop 22. For example, as illustrated, the tails 51 may be tied through the loading loop 22 preferably in a simple half-hitch knot 52. While a half-hitch knot 52 is shown, any sliding knot that can be locked from further sliding that is known in the art may be utilized. Further, the tying of the half-hitch knot 52 may be performed prior to inserting the filamentary sleeve 30 in the bore hole 81 or after.

Figure 6:
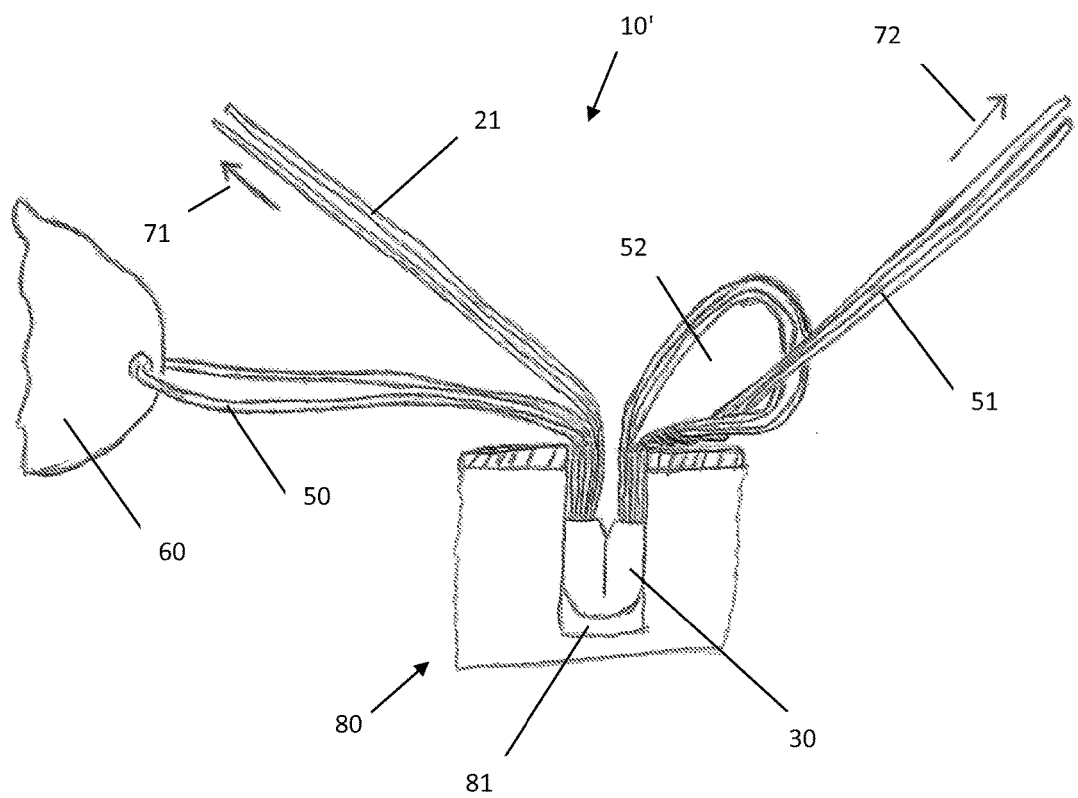
Figure 7:
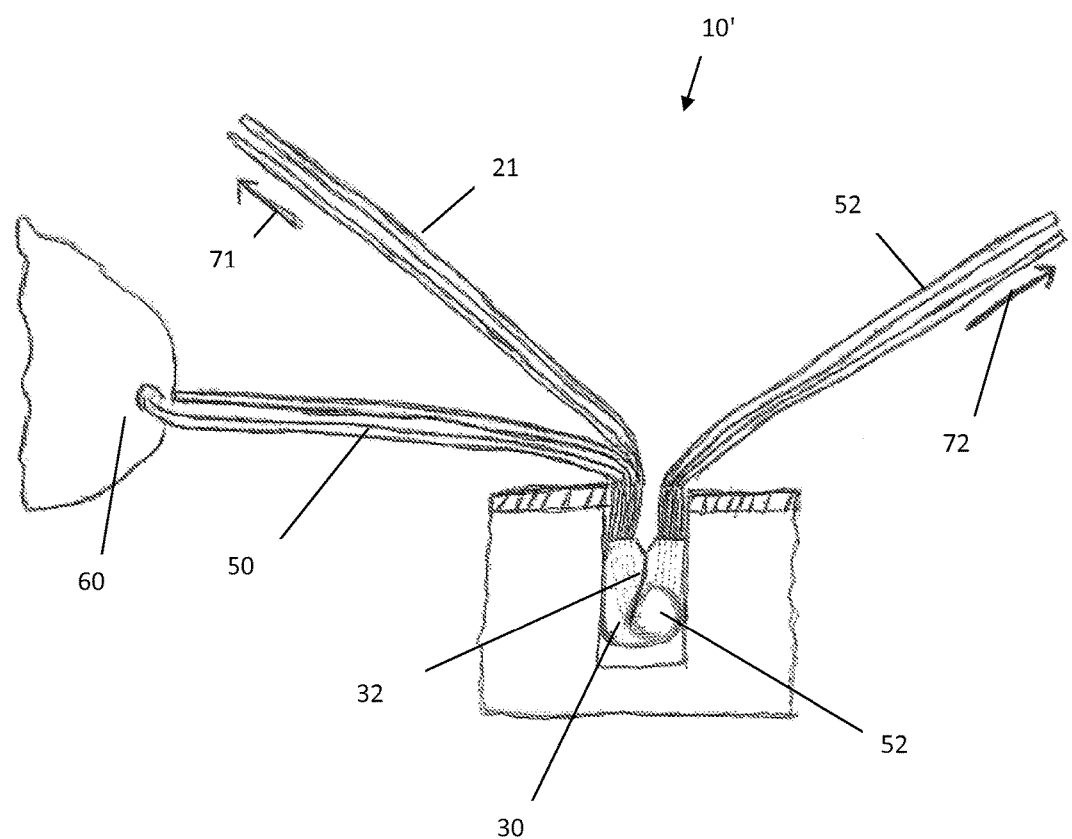

Referring to FIGS. 6 and 7, with the half-hitch knot 52 tied through the loading loop 22, the loading tails 21 are tensioned as demonstrated by arrow 71. Contemporaneous with the tensioning of the loading tails 21, the working tails 51 are tensioned as demonstrated by arrow 72. The tension on the loading tails 21 pulls the half-hitch knot 52 resulting in the sliding of half-hitch 52 toward the bore hole 81 and filamentary sleeve 30 as illustrated by FIG. 6, while the tension on the working tails 51 allows the working suture 50, and thus tissue 60, to be tensioned. Further, tension on the tails 51 can allow the half-hitch 52 to slide along the working suture 50, while suture 50 and tissue 60 are tensioned and drawn towards bone hole 81, while preventing the working tails 51, and half-hitch 52, to prematurely move into the bore hole 81 and sleeve 30. Further, the tension on the working tails 51 may contract the half-hitch knot 52 and allow the user to maintain appropriate tension on the working suture 50 and the tissue 60 while the half-hitch 52 is slid into the filamentary sleeve 30, as seen in FIG. 7.

Figure 8:
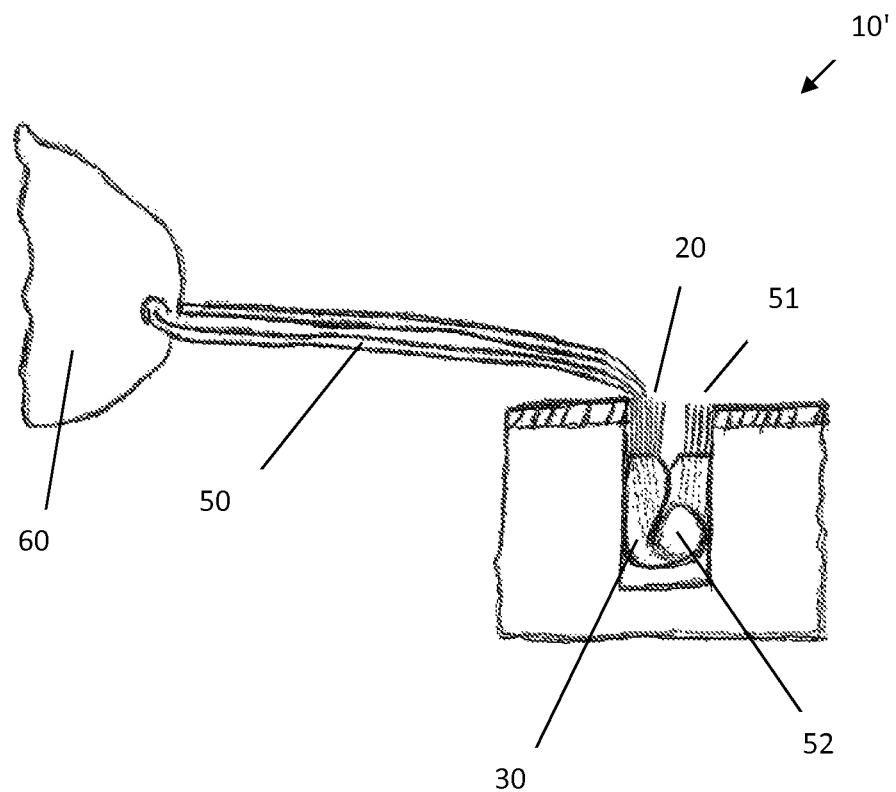

As the knot 52 enters into the pathway 33, the knot 52 may become trapped by the fold 32 (or other material of sleeve 30), at which point further tension on the working tails 51 and loading tails 21 further contracts the half-hitch knot 52, until the working suture 50 and sleeve 30 are fixedly secured with one another and the engagement is so tight that it is no longer capable of sliding, thereby effectively securing the tissue 60. Further, as the half-hitch 52 contracts and tightens, the material forming the knot 52 may become localized at a point, which further expands the filamentary sleeve 30 against the bore hole 81, providing added anchoring support. This mechanism may provide the user the ability to maintain the desired tension of the working suture 50 up until the half-hitch 52 is locked into position, thereby setting the desired tension into the working suture 50 and tissue 60. The working tails 51 and loading member 20 are trimmed close to the surface of the bone 80 resulting in a configuration as shown in FIG. 8 where the filamentary sleeve 30 is fixedly secured in the bore hole 81 and the half-hitch 52 fixedly secures the working suture 50, sleeve 30 and tissue 60 to one another and to the bore hole 81. Thus, as illustrated, a portion of the loading member 20 can remain within the filamentary sleeve 30.

In another embodiment, the present invention includes a system for the repair of soft tissue including at least one filamentary fixation assembly (including or in addition to a working suture 50), at least one instrument for insertion of the filamentary fixation assembly, and a surgical procedure. The surgical procedure may include instructions or protocol for using the filamentary fixation assembly and instrument to repair soft tissue. The protocol may include aspects of any of the above-discussed embodiments, though other variations are also envisioned within the scope of the present invention.

In an associated embodiment, the present invention includes a method of providing instructions or information to practice any of the various methods of performing soft tissue repair described herein. For example, the method may include supplying a surgical protocol, or like document, to provide step-by-step instructions for performing any of the method embodiments of the present invention.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of assembling a filamentary fixation assembly, comprising the steps of:
   obtaining a filamentary sleeve having a pathway therethrough, a loading member positioned through at least a portion of the pathway such that a loop portion of the loading member extends from a first end of the pathway and at least one loading tail of the loading member extends from a second end of the pathway, and a retriever member positioned through at least a portion of the pathway;
   engaging a working suture with the retriever member;
   tensioning the retriever member so as to position at least a portion of the working suture in the pathway and so that working tails of the working suture pass through the pathway and extend therefrom; and
   engaging the loop portion of the loading member with the working suture which includes tying the working tails into a sliding knot around the loading member.

2. The method of claim 1, further comprising the step of tensioning the loading member such that the sliding knot passes into the pathway.

3. The method of claim 2, wherein the retriever member includes a first end and a second end, the first end having a first loop configuration, the loading member includes a first end and a second end, the first end having a second loop configuration, and the filamentary sleeve including a first end and a second end, wherein the retriever member is positioned through the pathway of the filamentary sleeve such that the first loop configuration extends from the first end of the filamentary sleeve and the second end of the retriever member extends from the second end of the filamentary sleeve and the loading member is positioned through the pathway of the filamentary sleeve such that the second loop configuration extends from the second end of the filamentary sleeve and the second end of the loading member extends from the first end of the filamentary sleeve.

4. The method of claim 3, wherein the step of engaging the working suture with the retriever member includes passing the working tails through the first loop configuration.

5. The method of claim 4, wherein the tying step includes tying the working tails through the second loop configuration of the loading member and the tensioning of the loading member step includes pulling the second end of the loading member to pull the sliding knot into the pathway.

6. A method of assembling a filamentary fixation assembly, comprising the steps of:
obtaining a filamentary sleeve having a pathway therethrough and a loading member and retriever member being simultaneously disposed within the pathway;
engaging a working suture with the retriever member;
positioning at least a portion of the working suture in the pathway using the retriever member which includes tensioning the retriever member so that a free end of the working suture passes through a first end of the filamentary sleeve and out of a second end of the filamentary sleeve;
engaging the free end of the working suture with a portion of the loading member; and
tensioning the loading member so as to draw at least a portion of the free end and the portion of the loading member engaged to the free end into the filamentary sleeve from the second end thereof.

7. A method of assembling a filamentary fixation assembly, comprising the steps of:
engaging a working suture with a retriever member, the retriever member being disposed within a filamentary sleeve having a pathway therethrough;
tensioning the retriever member so as to position a portion of the working suture within the pathway and so that at least one working tail of the working suture extends from the pathway of the filamentary sleeve;
forming a sliding knot about a loading member with the at least one working tail of the working suture, the loading member being disposed within the pathway of the filamentary sleeve; and
tensioning the loading member so as to position the sliding knot within the pathway of the filamentary sleeve.

* * * * *